United States Patent
Chan et al.

(10) Patent No.: US 6,175,759 B1
(45) Date of Patent: Jan. 16, 2001

(54) CONTRAST AGENT FOR MULTISPECTRAL INFRARED TRANSILLUMINATION AND FLUORESCENCE OF TURBID MEDIA

(75) Inventors: Robert W. Chan, Amsterdam, NY (US); Robert Y. Levine, Carlisle, MA (US)

(73) Assignee: The United States of America as represented by the Secretary of the Air Force, Washington, DC (US)

( * ) Notice: Under 35 U.S.C. 154(b), the term of this patent shall be extended for 0 days.

(21) Appl. No.: 09/340,593

(22) Filed: Jun. 28, 1999

(51) Int. Cl.[7] .................................................. A61B 6/02
(52) U.S. Cl. ..................................... 600/431; 600/473
(58) Field of Search ................................ 600/431, 473, 600/475, 310, 317, 407, 425

(56) References Cited

U.S. PATENT DOCUMENTS

| | | | |
|---|---|---|---|
| 5,694,938 | * 12/1997 | Feng et al. | 600/425 |
| 5,803,582 | * 9/1998 | Stapleton et al. | 600/407 |
| 5,931,789 | * 8/1999 | Alfano | 600/473 |
| 6,009,340 | * 12/1999 | Hsia | 600/407 |

* cited by examiner

Primary Examiner—Teresa Walberg
Assistant Examiner—Quang Van
(74) Attorney, Agent, or Firm—William G. Auton

(57) ABSTRACT

A non-invasive multispectral energy system made up of a transilluminating radiating means that illuminates soft tissues that have been treated with a contrast agent using first and second non-IR illuminating signals to produce thereby a first and second near-IR multispectral images; means for optically combining the first and second near-IR multispectral images into a combined tissue image; and a means for processing the combined tissue image to detect cancer and tumors. The non-invasive multispectral imaging system uses a diode laser system that emits the first and second near-IR illuminating signals with wavelengths selected from a range between 750 nm and 1,000 nm as a radiating means and a CCD camera, which is placed in a location with the soft tissues between the CCD camera and the transilluminating radiating means. IR dyes and endogenous chromophores and fluorsphores enhance IR contrast and tumor sites. IR contrast agents such as Indeganine Green (ICG) are used.

10 Claims, 18 Drawing Sheets

Transmittance for heparinized undiluted human blood in oxgenated and deoxygenated states (5-mm path length).

Radial Distance from Photon Input (0.1 mm)

CONTRAST AGENT FOR MULTISPECTRAL INFRARED TRANSILLUMINATION AND FLUORESCENCE OF TURBID MEDIA

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to infrared spectroscopy and, more specifically, the invention pertains to a Contrast Agent for multispectral infrared transillumination and fluorescence of turbid media.

This invention is for non-invasive multispectral IR absorption and fluorescence measurement system for the detection of blood related abnormalities in tissue. An FDA-approved contrast agent, tailored to the measured spectral range, is introduced intravenously to provide both absorption and fluorescent contrast in tissue. While the full scope of eventual uses will emerge through clinical experience, two immediate areas of application are for the detection of breast cancer and internal bleeding.

SUMMARY OF THE INVENTION

The present invention includes a non-invasive multispectral energy system made up of a transilluminating radiating means that illuminates soft tissues that have been treated with a contrast agent using first and second non-IR illuminating signals to produce thereby a first and second near-IR multispectral images; a means for optically combining the first and second near-IR multispectral images into a combined tissue image; and a means for processing the combined tissue image to detect cancer and tumors.

The non-invasive multispectral imaging system uses a diode laser system that emits the first and second near-IR illuminating signals with wavelengths selected from a range between 750 nm and 1,000 nm as a radiating means and a CCD camera, which is placed in a location with the soft tissues between the CCD camera and the transilluminating radiating means.

To function IR dyes and endogenous chromophores and fluorsphores enhance IR contrast and tumor sites. Intravenous IR contrast agents such as Indocyanine Green (ICG) are used.

It is an object of the invention to provide a system for early detection of breast cancer and internal bleeding. It is another object of the invention to provide a non-invasive multispectral IR tissue imagery system.

These and many other objects and advantages of the present invention will be readily apparent to one skilled in the pertinent art from the following detailed description of a preferred embodiment of the invention and related drawings.

DETAILED DESCRIPTION OF THE PREFERRED EMBODIMENT

The present invention is a non-invasive multispectral IR absorption and fluorescence measurement system.

Figure 1:
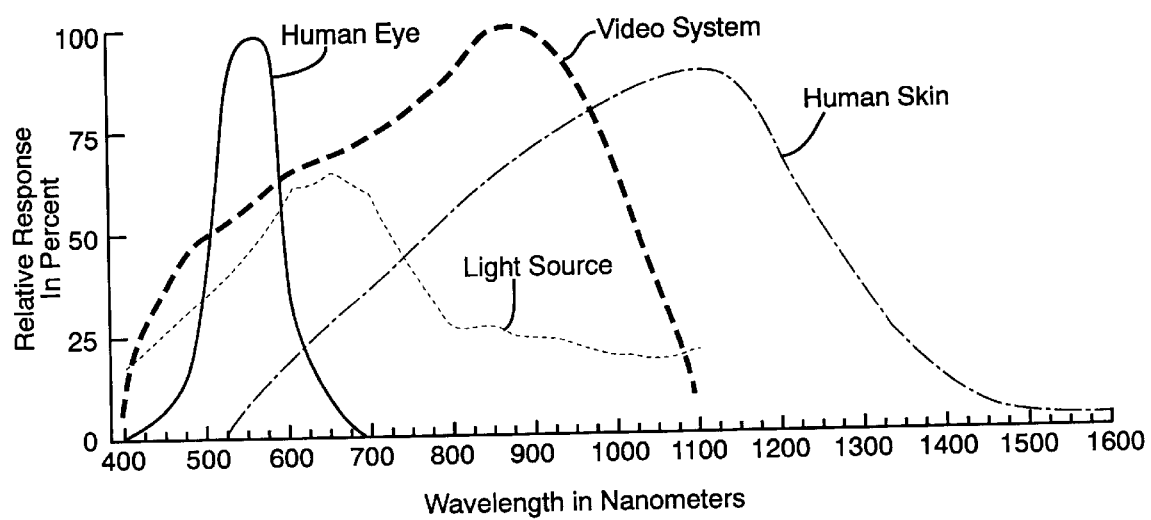
FIG. 1 is a chart of human tissue transillumination and imaging system response spectra.
Figure 2:
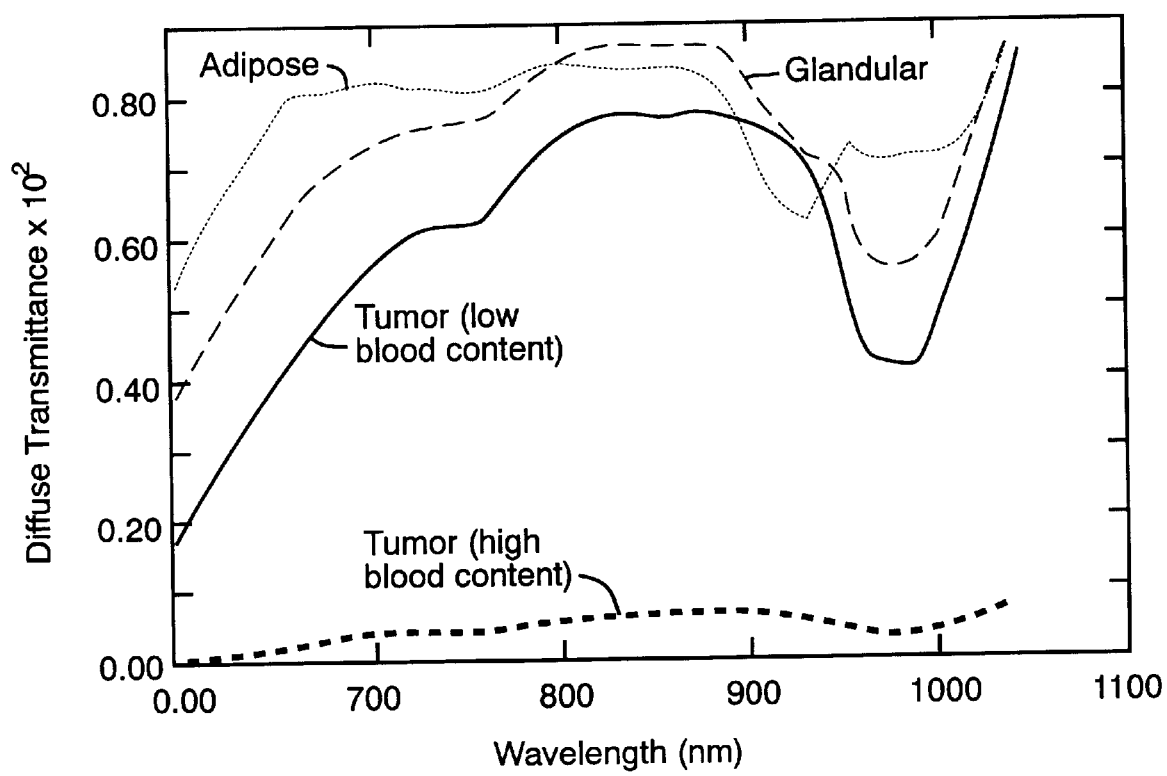
FIG. 2 is a chart of diffuse transmittance of breast tissue and tumors of variable blood concentration.
Figure 3:
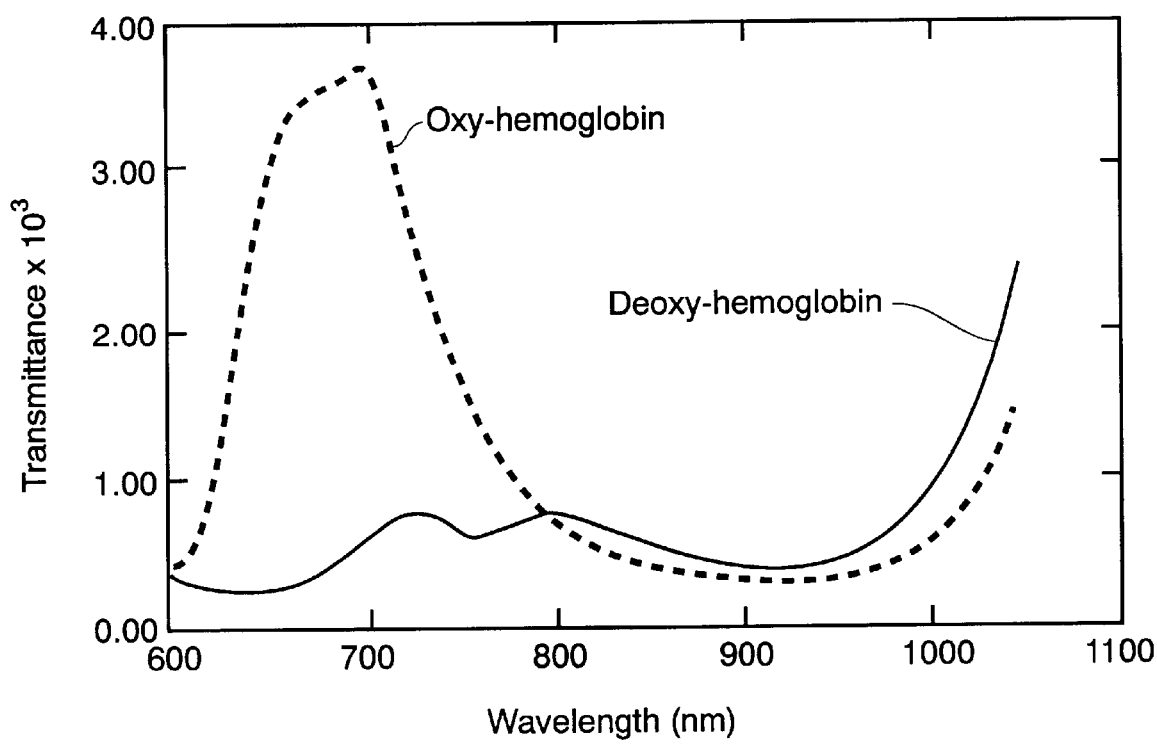
FIG. 3 is a chart of spectral transmittance of oxygenated and deoxygenated hemoglobin.

The attraction of near-IR light for soft tissue imaging is seen from FIG. 1, which demonstrates a window of relative penetration in the 700 nm–1200 nm wavelength range. The mechanism for transilluminated light detection of tumors has been studied since the technique was first proposed in 1929, and rediscovered for infrared in the 1980's. A tumor is often observed as a dark spot, which may result from an accumulation of blood in the tumor periphery. FIG. 2 contains the diffuse transmittance spectra of common breast tissues, in which it is seen that transmittance decreases significantly for a vascular tumor. This correlates with red blood cell estimates in Table I, showing that red blood cell concentration at the edge of a tumor may be a four-fold factor of the concentration in other tissues. There is also evidence that tumors are observable from the ratios of IR and red light images due to the distinct spectral characteristics of cancerous tissues. FIG. 3 contains the spectral transmittance curves of oxygenated ($HbO_2$) and deoxygenated (Hb) hemoglobin, indicating that $HbO_2$ is much more transmissable below 800 nm than Hb. This suggests that the ratio of the 900 nm and 700 nm transmission images is a sensitive measure of the dominant hemoglobin type in the tissue. The distinction between $HbO_2$ and Hb near-IR spectral properties is the basis for external pulse oximetry. It has been speculated that blood vessels near cancerous tissue have more deoxy-hemoglobin due to rapid cellular metabolism; a fact that could be useful to discriminate between cancerous and benign tissues. In addition, the non-invasive measurement of oxy-hemoglobin content in tumors is important for therapeutic monitoring and evaluation of prescribed chemo- and radio-therapies.

TABLE 1

Average red blood cell concentration.

| Tissue | RBC (mm/g) |
|---|---|
| Normal | 4.2 |
| Fibroadenoma | 5.4 |
| Carcinoma (tumor) | 4.9 |
| Carcinoma (edge) | 16.0 |
| Peripheral | 9.2 |

Figure 4:
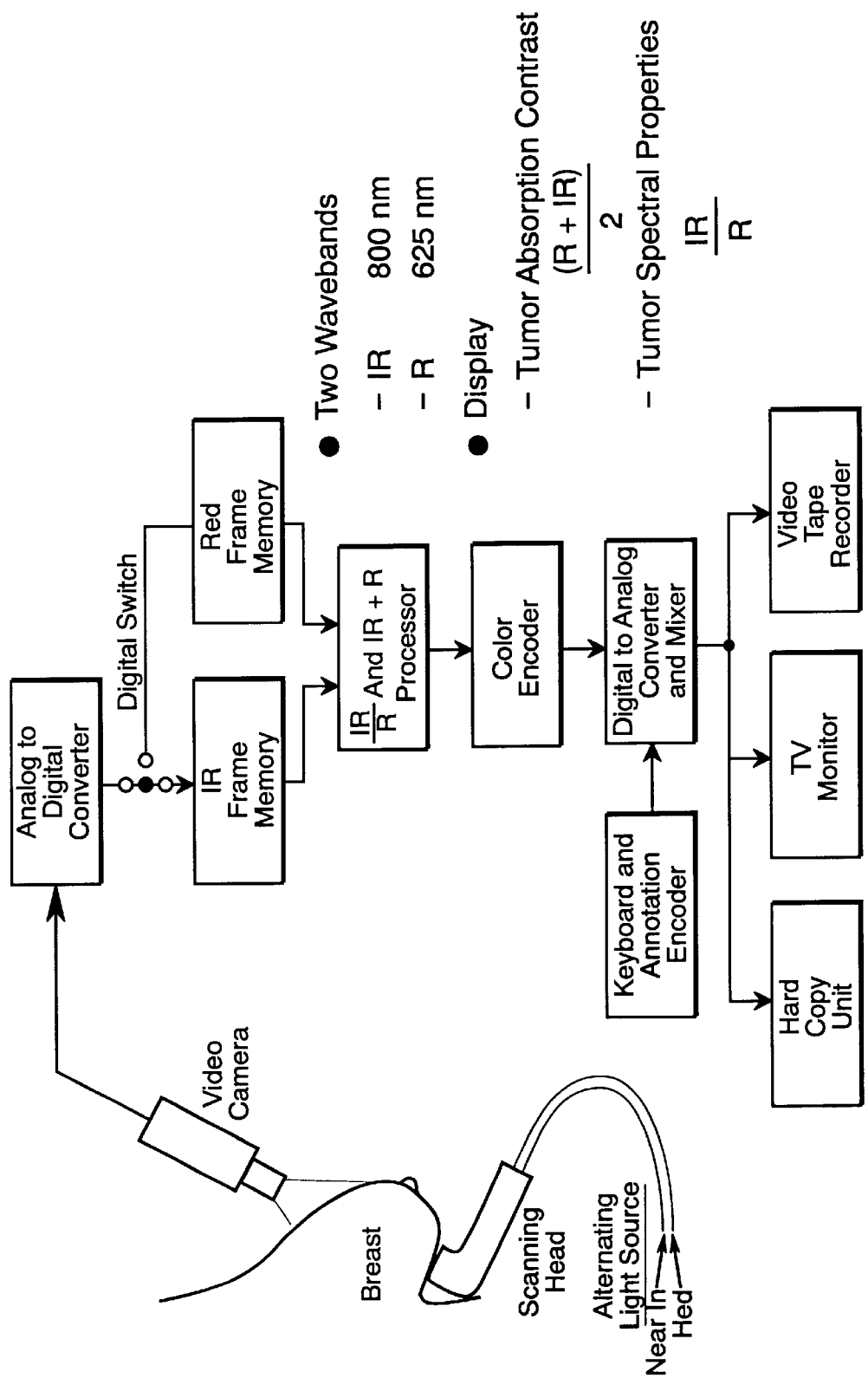
FIG. 4 is illustration of the preferred embodiment of the present invention.

Traditional infrared lightscanning for breast cancer involves the measurement of a breast image resulting from the placement of red and near-IR light sources under the breast. As seen in FIG. 4, the two images (at 625 nm and 800 nm) recorded on the opposite side are combined to increase the lesion detection probability. As practised in the 1980's, IR lightscanning failed as a diagnostic technique in the United States. Among the reasons for this is that cancer detection and false alarm rates for lightscanning, at about 60% (non-palpable), are inferior in the general population to X-ray mammography. Observable features in the near-IR are insufficient to discriminate among cancerous tissues, benign tumors, fibrous tissues, and other breast conditions unless the lesion is large enough to be easily seen by X-rays. This is primarily because scattering effects dominate in the IR, with the result that subtle contrasting features are indistinguishable for light propagation through more than 3 cm of tissue. It should be emphasized, however, that the technique does detect breast cancer; and is particularly useful in circumstances where X-ray mammography is unavailable or inappropriate. For example, because of the deep tissue penetration of near-IR light, it is a viable alternative for highly glandular dense breasts which are opaque to X-rays. Mammographically opaque breasts are more common in younger women for whom the dangers of accumulating X-ray radiation suggests the need for an alternative imaging technique.

The sensitivity of IR light to blood concentration, demonstrated in FIG. 2, suggests the application of IR imaging to the detection of internal bleeding. The condition, which is deadly and hard to diagnose, is often detected in the abdomen by the measurement of blood flow from a test incision. In an effort to decrease the lethality of battlefield wounds, DARPA is currently funding the development of portable diagnostic tools to provide better allocation of medical resources. Due to the thickness of tissue traversed by light to create an absorption image, the application of IR imaging to internal bleeding detection requires fluorescence measurements at the emission wavelength of a blood-borne fluorphore. We view these measurements as a natural extension of IR transillumination imaging, which also has application to tumor detection.

This project involves the enhancement of near-IR imaging to address the shortcomings mentioned above. The distinctive features of cancerous tissue in the IR range may be more evident if multispectral images are optimally combined. Scattering effects can be modeled with Monte Carlo simulation to derive deblurring algorithms which take advantage of multiple images at different wavelengths. Finally, contrast agents with distinct near-IR spectral properties are known to accumulate around tumors. In combination with appropriate multispectral image processing, these agents provide a mechanism to discriminate cancerous tissue. If the contrast agent fluoresces, we obtain an independent detection measurement through the application of a laser and detector specific to the excitation and emission wavelengths. In the past year we have tested the feasibility of applying multispectral imaging, Monte Carlo simulation, and near-IR contrast agents for in-vitro detection of cancer. The measurements and algorithm development were performed at Lincoln Laboratory using an experimental apparatus to image breast biopsies in the near-IR range. The results of that effort, described in the following sections, suggest that we are now ready to start an in-vivo phase of experimentation, simulation, and algorithm development. We are proposing to augment the absorption measurements with external near-IR in-vitro and in-vivo fluorescence detection. The experiments and simulation will be designed for a proof-of-concept verification of both tumor and internal bleeding detection with the apparatus.

The invention is grouped into four parallel activities, 1) biological experimentation, 2) simulation, 3) algorithm development, and 4) tumor-specific antibody conjugation. The biological experiment, located at the Dana-Farber Cancer Institute, involves using the Lincoln apparatus to image live rats with developing carcinoma and injected blood pools. Monte Carlo simulation will be used to define experimental parameters and guide the development of multispectral cancer discrimination algorithms. The associated data processing and algorithm development will be performed at Lincoln Laboratory. This discussion describes a promising new component of the research project; that is, the enhancement of IR imaging by conjugation of dyes to tumor-specific antibodies. We are in a unique position to leverage a forefront interdisciplinary effort in cancer research. The overall goal of the project is the identification of an FDA-approved hear-IR contrast agent and associated discrimination algorithms for the detection of early-stage breast cancer and deep tissue internal bleeding with IR light. The trade-off curves and experimental results will define specifications for a non-invasive, portable instrument for IR characterization of blood flow anomalies, such as occuring with vascular tumors or internal bleeding.

The biological component of this invention consists of the in-vivo multispectral IR transillumination and fluorescence of tumors and blood pool injections in rats. We are working in collaboration with Drs. Beverly Teicher and Gulshan Ara of the Pharmacology Department of the Dana-Farber Cancer Institute. Both of these individuals are leading researchers in the physiology of tumor development, who have committed their own laboratory resources to the project based on a series of discussions with the Lincoln group on this proposal. The experimental apparatus, which was built at Lincoln Laboratory for a 1993–1994 project in breast biopsy imaging, has been used during the past year for feasibility studies of this proposal. The base of the apparatus illuminates a stage upon which the tissue sample is placed. The transilluminating photons are directed through near-IR bandpass filters in the 750 nm–1000 nm range at 40 nm increments, recorded with a Spectrasource MCD-1000 CCD camera, and stored in a computer for processing. A vascular malignant tumor of diameter less that 1 cm, indicated in the figure, is seen as a darker region most clearly on the 750 nm image. Note the gradual change in the images as the near-IR wavelength of the photon is increased. It is expected that multispectral imaging would enhance discrimination of the tumor because of the different spectral behavior of cancerous and normal tissues. As discussed in the text section, wavelength-dependent scattering of the transilluminating photons causes image blurring which completely dominates the subtle image variation in FIG. 8 as photon wavelength is increased. The proposed fluorescence experiment involves the augmentation of the set-up in FIG. 4 using a diode laser (mW) and a narrow-band filter.

In addition to deriving deblurring filters to remove scattering effects, we have investigated the use of near-IR contrast agents to enhance spectral differences between tumor and normal tissues. The goal is to discover an agent, which accumulates at the tumor site, with an absorption edge in the 750 nm–1000 nm range. This would increase differences among the images, as well as between cancerous and normal tissue regions on each image. In the course of our in-vitro experiments this year we discovered a promising drug, Indocyanine Green (ICG), which has been provided to us for free by the leading manufacturer, Benton-Dickenson, Inc. The FDA-approved drug is used for retina imaging and heart imaging. Note from the absorption spectrum that ICG has a desired absorption edge at 805 nm; suggesting distinguishing spectral structure in the measurement range. Motivated by a recent report in the literature, we are currently investigating the use of a laser for in-vivo excitation of ICG in a tumor in combination with the proposed absorption measurements. Our modeling results, discussed below, are promising for the detection of ICG fluorescence from deep tissue (≈8 cm) accumulation of blood arising from either vascular tumors or internal bleeding. Using the discrimination algorithms, we have been able to detect $\leq$5 gm of ICG through 2 cm of tissue. This is significant because from in-vivo fluorescence measurements in rats, reported by a group at the University of Pennsylvania, we estimate ICG tumor accumulation of about 2 $\mu$gm. In addition, as discussed in the next section, a 1ml blood pool at the recommended ICG dosage in a 80 kgm patient corresponds to a detectable 6 $\mu$gm of ICG. We are confident with further refinement of our experimental technique and processing algorithms we will be able to detect below this threshold amount of ICG from the near-IR image set.

Figure 5:
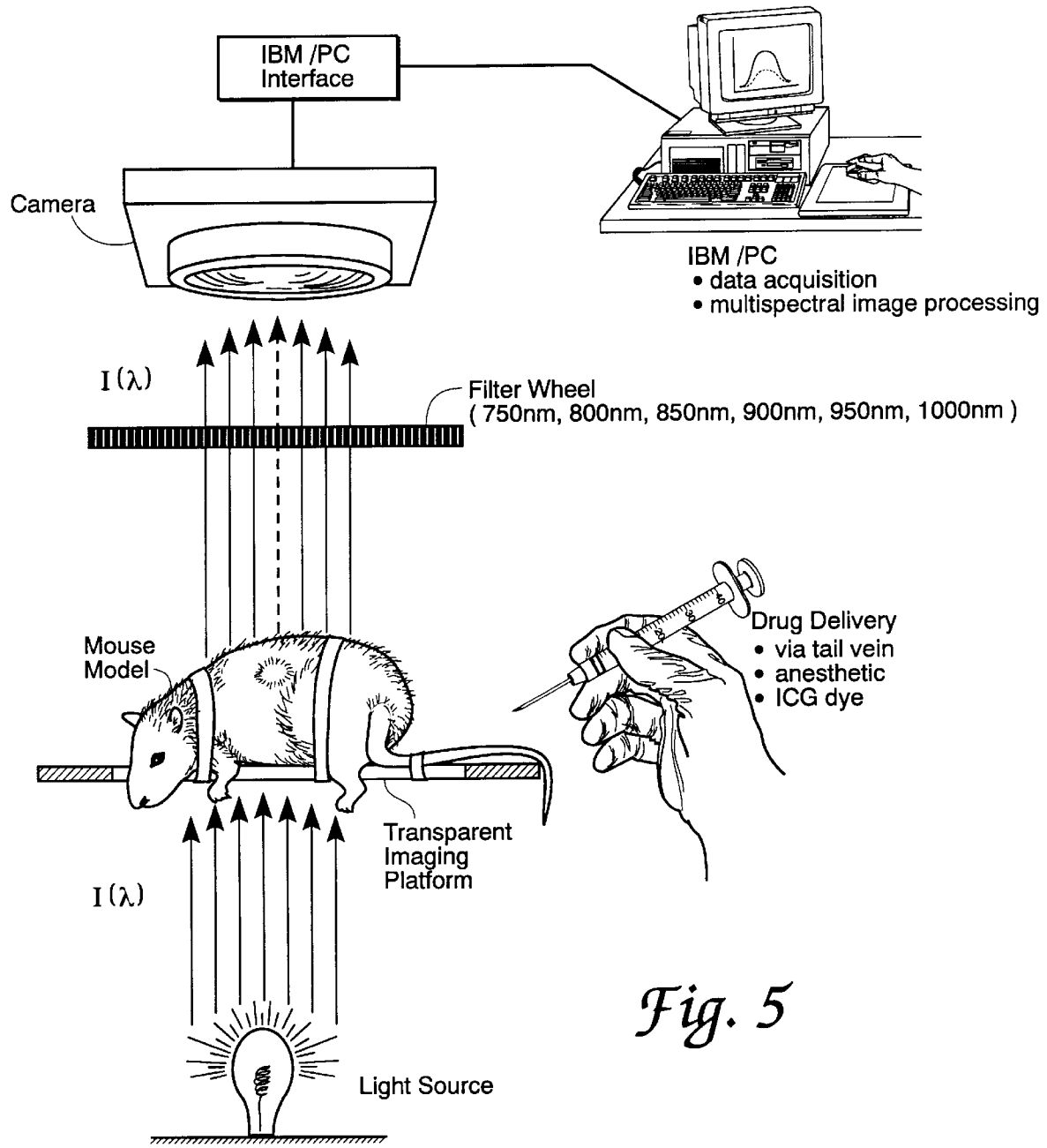
FIG. 5 is an illustration of the Near-IR transillumination test of the present invention.
Figure 6:
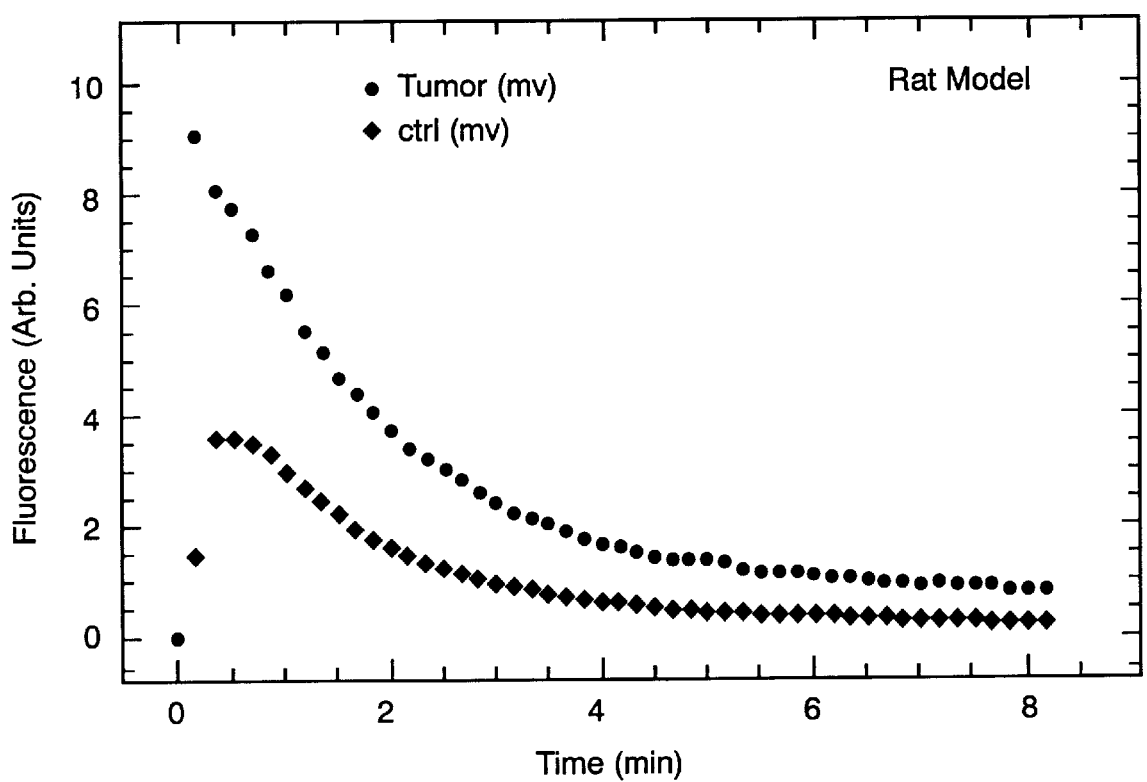
FIG. 6 is a chart of fluorescence signal vs. time after ICG injection in the mouse of FIG. 5.
Figure 7:
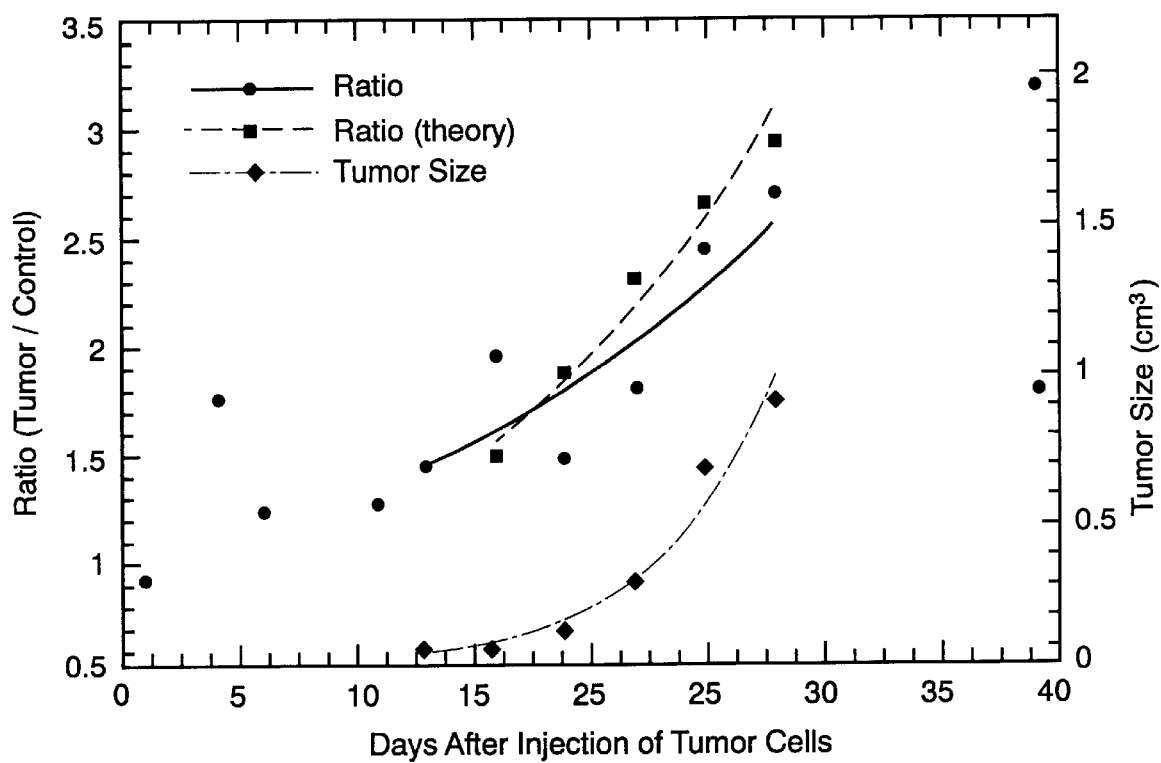
FIG. 7 is a chart of fluorescence signal ratios vs. days after cell injection.
Figure 8:
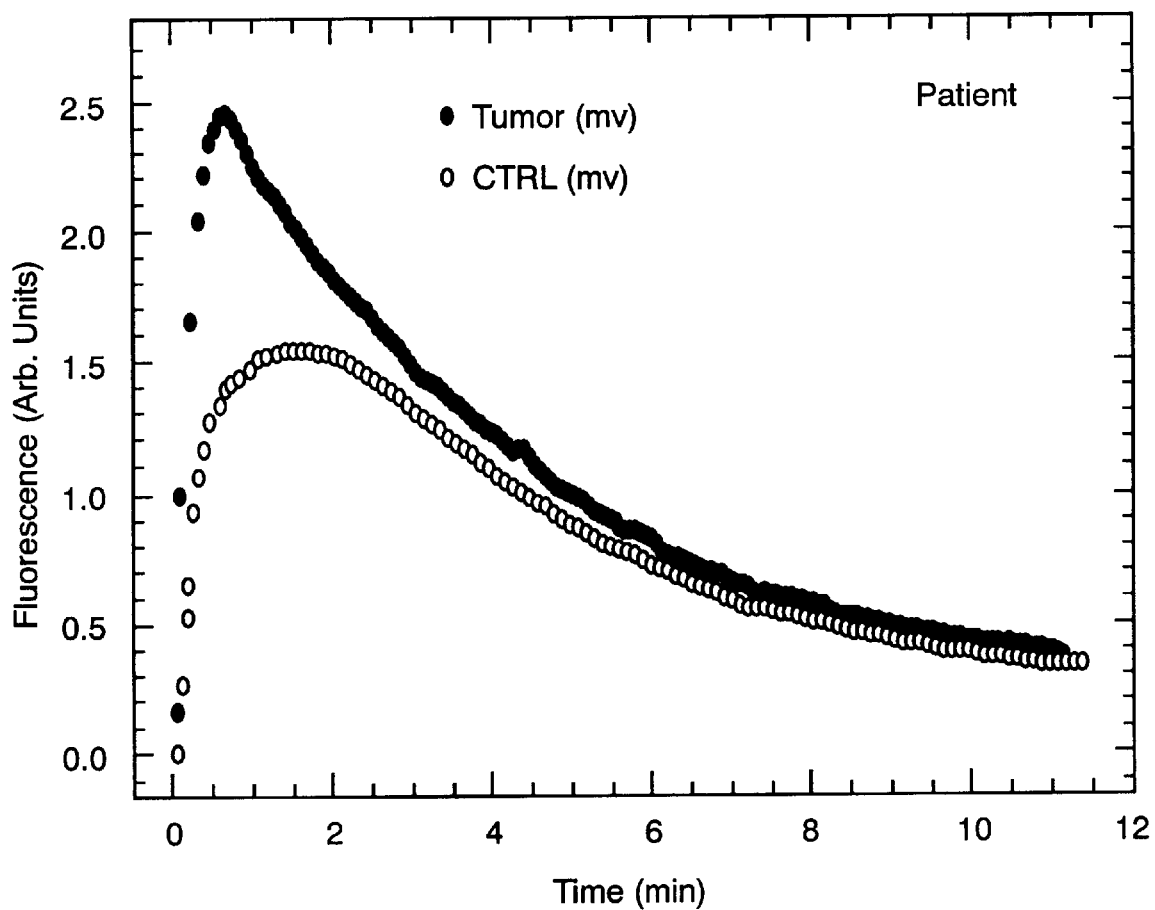
FIG. 8 is a chart of accumulation of ICG in human tumors vs. time.

FIG. 5 contains a schematic of the proposed experiment using the Lincoln Laboratory apparatus at the Dana-Farber Cancer Institute. Cancer cells will be introduced into the hind leg of a rat, leaving the other leg for control measurements. We will then take near-IR multispectral images of the developing tumor in the anesthetized animal periodically as contrast agent is injected into the tail vein. The imaging of a blood pool will be tested by the direct injection of minute quantities of an ICG/serum mixture in the rat. The complete set of time-sequenced IR images, with and without ICG, will be stored in the computer for processing at MIT Lincoln Laboratory. As mentioned above, there is evidence of ICG accumulation in rat tumors from fluorescence measurements reported in the literature. FIG. 6 is a plot of fluorescence signal versus time after ICG injection from both the control and tumor-bearing legs of a rat. Fluorescence in the subcutaneous tumors was induced by a laser at 805 nm, which is the excitation frequency of ICG. From a calibration curve in the same publication, we estimate an ICG concentration of 2.1 $\mu$gm/ml. FIG. 7 contains the ratio of the fluorescence signal in the tumorous leg to healthy leg as the tumor develops. Post-surgical examination of the tumors revealed that tumor size was correlated with the fluorescence signals. From FIG. 7 we estimate that 2 $\mu$gm of ICG accumulated in 1 cc tumors after about 25 days of growth. FIG. 8 contains fluorescence measurements from breast cancer patients after injection of ICG at a recommended dosage of 400 $\mu$gm/kgm (BW). These results demonstrate the exciting possibility that ICG accumulated in human breast tumors, and was observable by fluorescence measurements. We are planning the addition of a fluorescence measurement capability to the experimental apparatus for application to both tumor and internal bleeding detection. The ICG in a tumor or blood pool will be excited by an 780 nm gallium arsenide diode laser. The fluorescent emission at the surface will be filtered at 835 nm before detection in the CCD camera. We will also perform spectral reflectance measurements without the bandpass filter in order to test for discrimination features in the reflectance spectrum. Optimum detection and localization of breast tumors with IR light will most likely result from a combined absorption-fluorescence measurement after ICG injections. The key issues are 1) the tumor or blood pool size at which sufficient ICG accumulation occurs for detection and discrimination, and 2) the effects of photon scattering on tumor detection as it relates to tumor depth and breast condition. The goal of the experiment is the application of multispectral discrimination for the detection of tumors at the onset of abnormal vascular development before metastases have occurred.

Indocyanine Green is a useful IR contrast agent because of the distinctive spectrum in the 750 nm –1000nm range. There are, however, endogenous IR chromophores such as oxy-hemoglobin and cell mitochondria which are specific to tumor structure and metabolism. Our approach to endogenous chromophore detection is three-fold: 1) generalize the discrimination algorithms to use chromophore spectra for detection with IR transillumination, 2) detect concentrations with fluorescence measurements, and 3) direct needle and histological measurements of in-vitro and in-vivo chromophore concentrations. Dana-Farber is providing a needle oximeter for in-vitro oxygen measurements, which will correlate with detection of $HbO_2$ by absorption and fluorescence. In addition to our goal of optimum tumor or blood pool detection, correlated measures of oxygen concentration could have other applications such as therapeutic monitoring of chemotherapies or assessments of shock. After a sequence of measurements consistent with the animal care protocol at Dana-Farber, a histological and spectrophotometric measurement of the tumor tissue will provide data on dye and endogenous chromophore concentrations in the tumor. In addition to the in-vivo IR images and histological examination, independent spectrophotometric measurements of all relevant compounds (dyes, $HbO_2$, Hb) will be obtained as inputs to discrimination and imaging algorithms.

Figure 9:
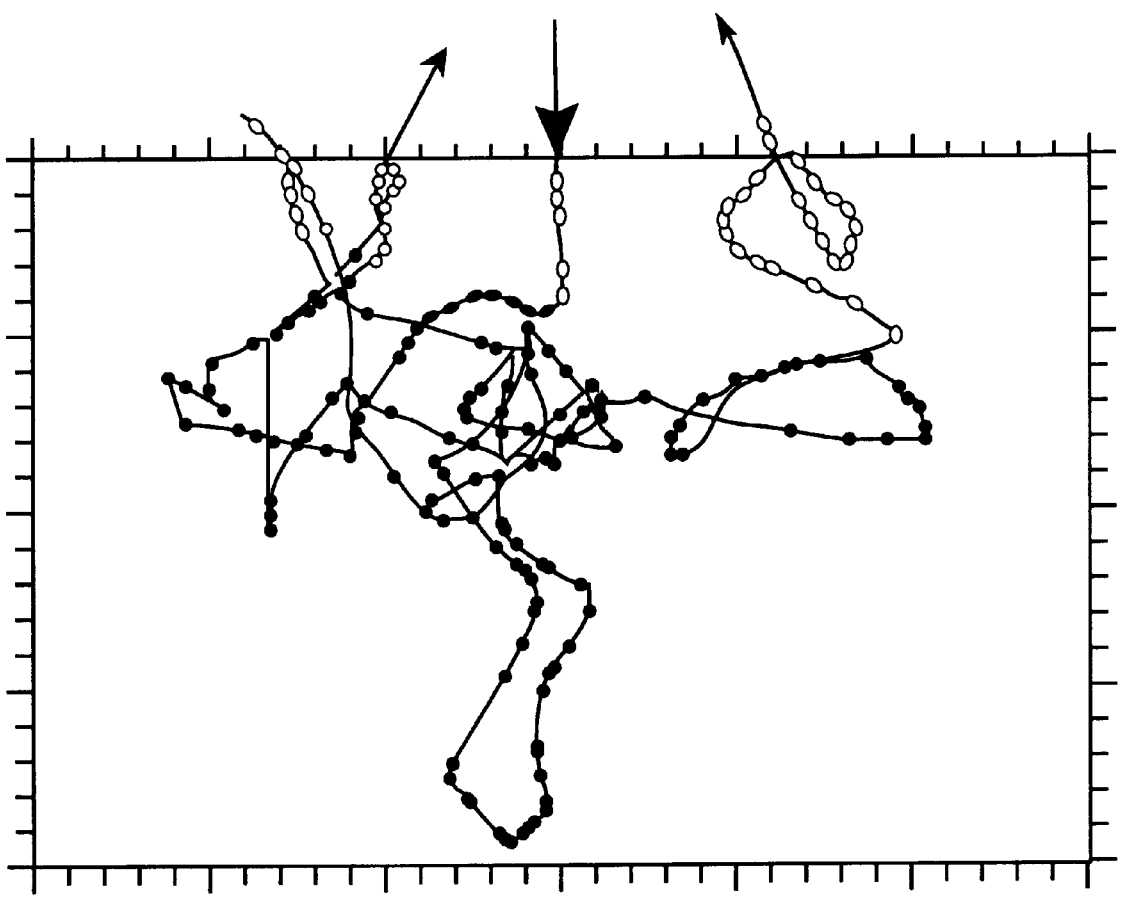
FIG. 9 is a chart of Monte Carlo Codes for near IR photon propagation through tissue.

During the in-vitro phase of this project, we obtained Monte Carlo codes which simulate the propagation of near-IR photons through tissue. The software, which was developed at the M.D. Anderson Cancer Center in Houston, Tex. (see FIG. 9), has input optical constants obtained by diffuse reflectance and transmittance measurements. We originally applied the codes to characterize the scattering effects of normal breast tissue on IR biopsy images with tumors. Monte Carlo simulation is an integral part of the in-vivo phase of experimentation in two areas; 1) derivation of deblurring filters and 2) characterization of contrast agents in tumors observed through IR imaging.

Figure 10:
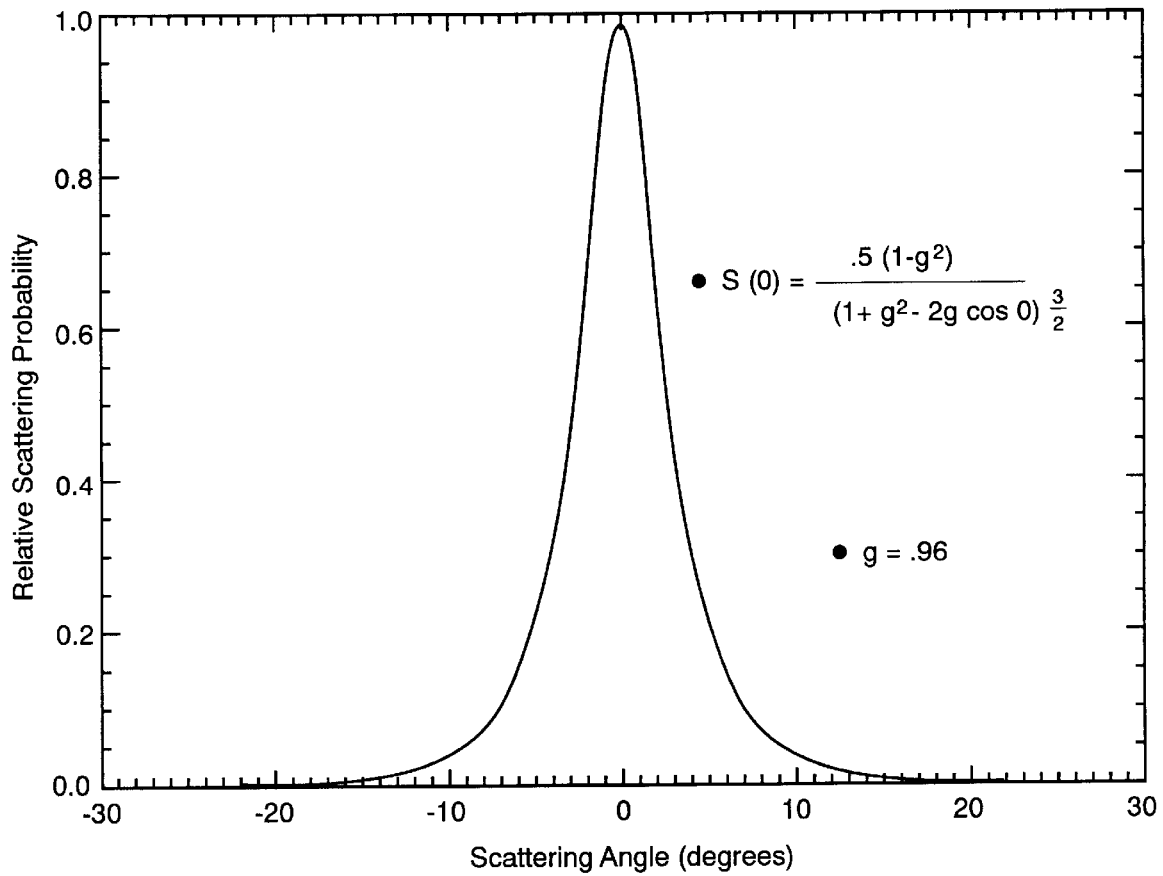
FIG. 10 is a chart of the Henyev-Greenstein scattering function for a forward scattering g-value of 0.96.
Figure 11:
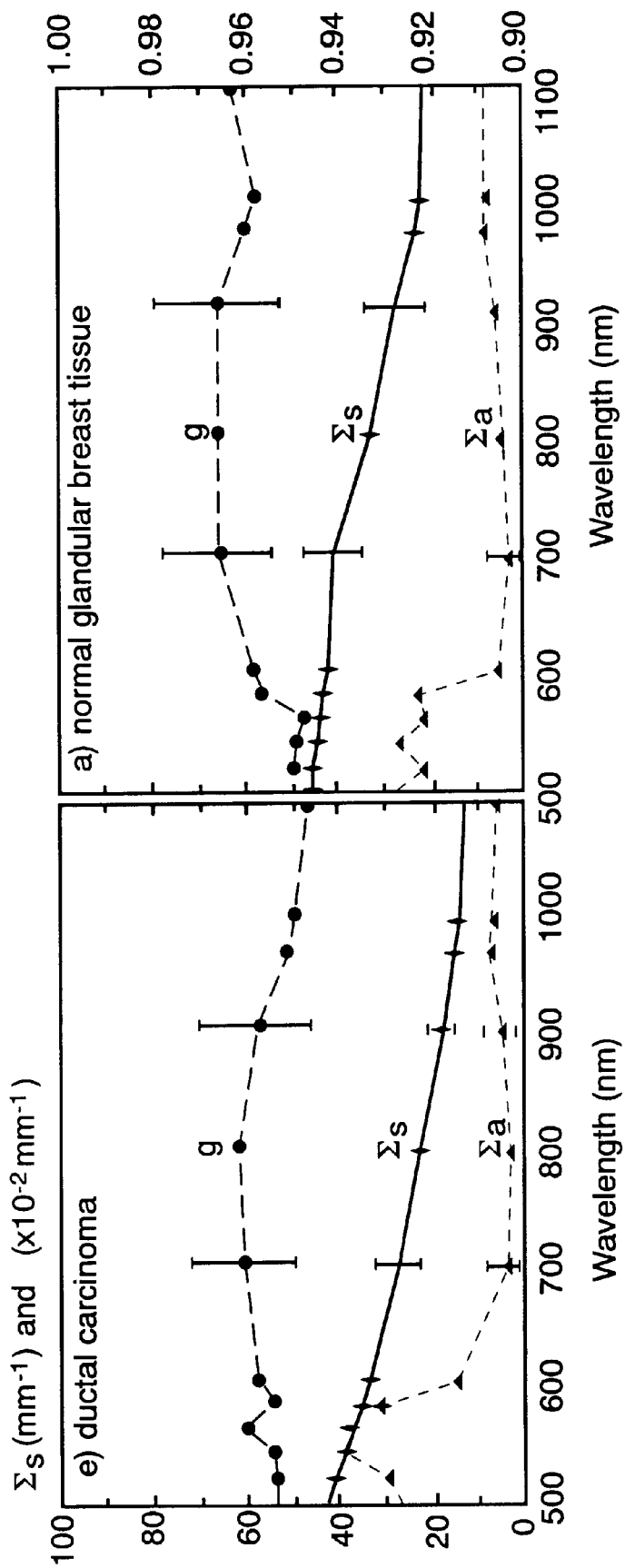
FIG. 11 is a chart comparing Near-IR optical characteristics of cancerous and normal tissue.

The three wavelength-dependent parameters describing photon propagation through turbid media are the absorption coefficient $\Sigma_a(\lambda)$, scattering coefficient $\Sigma_\alpha(\lambda)$ and the Henyey-Greenstein scattering parameter $g(\lambda)$. The absorptinog and scattering coefficients enter into the simulation by determining the probability of absorption and scattering as the photon steps through the calculation grid. The Henyey-Greenstein scattering parameter, which determines the angle into which the photon is scattered at a grid point, has a range [0,1] with 0 and 1 corresponding to isotropic and forward scattering, respectively. The Henyey-Greenstein scattering function for breast tissue, typically with a forward scattering g-value of 0.96, is shown in FIG. 10. From measurements on excised breast tissue, the optical parameters for normal, cancerous, and fibrous tissues have been determined. FIG. 21 contains the near-IR spectral measurements of $\Sigma$, $\Sigma_s$, and g for cancerous and normal breast tissue. Note the weak wavelength dependence of these parameters for both tissue types, which was a motivating factor in our search for contrast agents like ICG.

Figure 12:
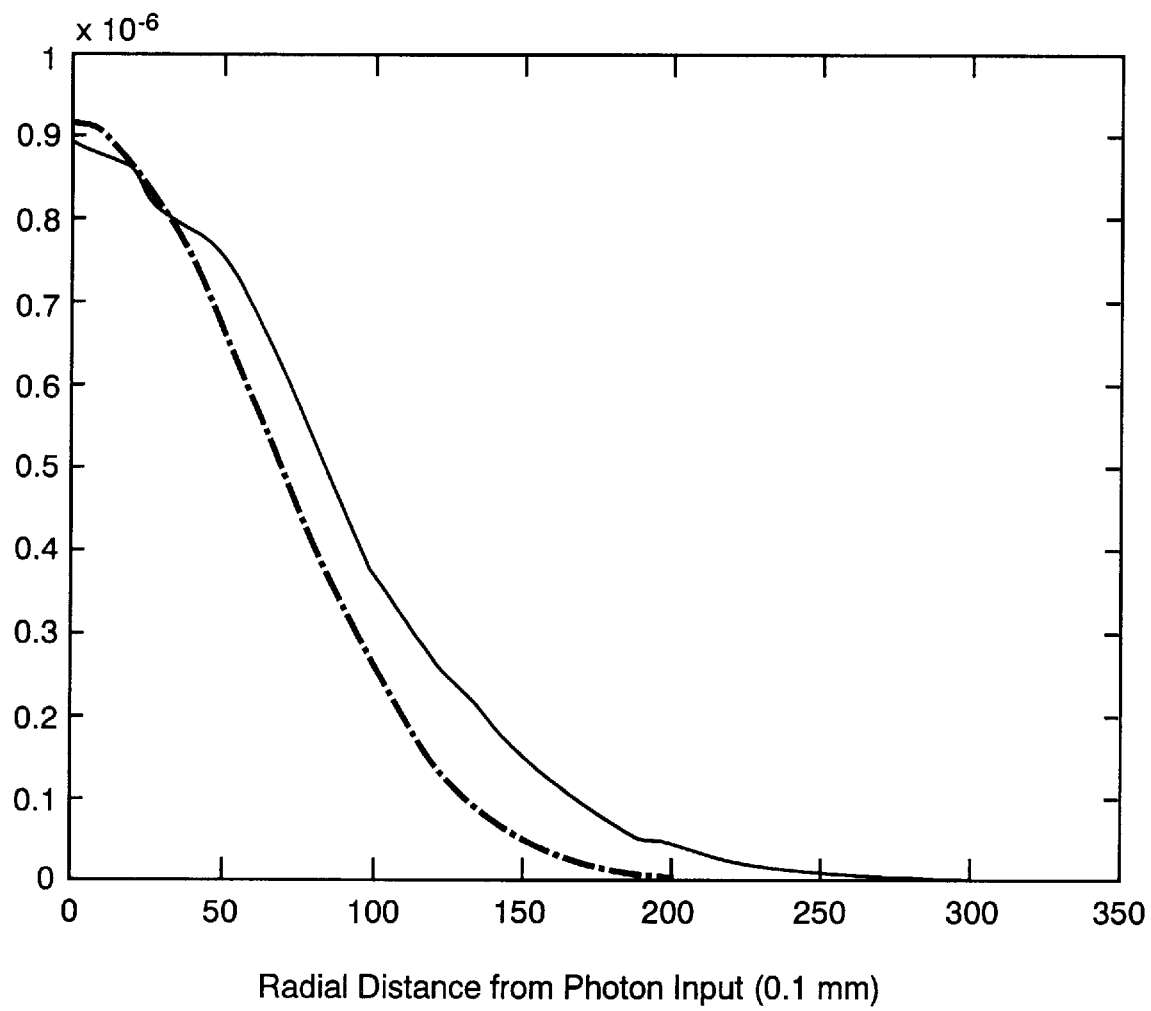
FIG. 12 is a chart of Monte Carlo simulated scattering of 750 nm propagation through tissue.

During the past year we generated depth-dependent multispectral kernel for photon scattering in normal breast tissue from the data in FIG. 1 and the M.D. Anderson codes. FIG. 12 contains the scattering kernel resulting from 3 cm of normal breast tissue for 750 nm photons, which was computed by the application of the codes to the propagation of one million photons. The kernels, computed for each wavelength, were applied to the breast biopsy images to simulate the effects of photon scattering through 3 cm of normal tissue after interaction with the tumor. As can be seen in FIG. 3, the biopsy image is significantly blurred due to the scattering-dominant media. This motivates the development of a bank of depth-dependent deblurring filters, which can be interactively sequenced to focus the underlying structures at various depths. These structures include wavelength-dependent spots due to contrast agent accumulation. Preliminary work on deblurring filters, which will be generalized to include spectral properties, is discussed below.

Recently the absorption spectrum of ICG in serum was applied to simulate the effect of scattering through normal tissue on an accumulated concentration of dye. FIG. 4 contains the blurred image of a 3.0 mm$^2$ blood pool through 1.0 cm of normal tissue with and without ICG at a concentration $10^{15}$ molecules/cm$^3$. The images are obtained by applying Monte Carlo calculated scattering kernels of the type in FIG. 2 to the photon output through ICG. Note the contrast enhancement resulting from the intravenous ICG injection. By multiple calculations of the type in FIG. 4, we derived trade-off curves of spot contrast versus dye concentration and tissue thickness shown in FIG. 5. The trade-off curve is defined as spot intensity contrast versus the product of ICG density and spot thickness (pd), which as discussed in the next section is the appropriate parameter to measure the optical effect of ICG. The trade-off algorithms will be applied after multispectral discrimination and deblurring to 1) monitor the effectiveness of the imaging algorithms and 2) establish detection thresholds for dye accumulation in tumors. Clinicians at the Dana-Farber Cancer Institute have suggested that the computation of threshold concentrations may have application to therapeutic monitoring of chemotherapy agents. In addition to the modeling of contrast agents, the trade-off curves will be computed for endogenous chromophores alone and in combination with other agents. The determination of concentration thresholds will help define experimental parameters such as drug dosage and camera exposure time.

The application of IR imaging to internal bleeding requires fluorescence measurements of deep tissue blood accumulation. FIG. 6 shows the experimental set-up for the fluorescence detection of a blood pool through excitation with a 780 nm 3 mW gallium arsenide laser diode and the subsequent measurement of 835 nm emitted light at the surface. We performed modeling calculations of the emitted photon flux assuming point-source diffusion of the light from the surface, stimulated and spontaneous decay of excited ICG molecules, and point-source propagation of 835 nm light to the surface. The parameters for the simulation included a $\phi_0 = 1.2 \times 10^{16}$ sec$^{-1}$ photon rate at the surface, an absorption coefficient $\Sigma_\alpha^{-1} = 33$ cm, scattering coefficient $\Sigma_s - 1 = 0.1$ cm, the ICG excitation cross section $\sigma = 1.3 \times 10 - 15$ cm2, and a diffusion model extinction coefficient $\Sigma - 1 = 1.05$ cm. The surface fluence at a distance $\chi$ from the laser input is then given by $$I = \frac{c\Gamma}{4\pi D} \frac{N_0}{2} \frac{2\sigma\phi}{\Gamma + 2\sigma\phi} \frac{e^{-K\sqrt{x^2+d^2}}}{\sqrt{x^2+d^2}} e^{-\Gamma_c t} e^{-(\Gamma+2\sigma\phi-\Gamma_c)t}, \quad (1)$$

where $\Gamma = 109$ sec$-1$ is the ICG decay rate, $D = c/3(\Sigma s + \Sigma \alpha)$ is the diffusion constant, N0 is the total number of ICG molecules in the blood pool at depth d, $\Gamma c = 1/300$ sec$-1$ is the body ICG removal rate, and $\phi$ is the external photon fluence at the blood pool depth;

$$\phi = \frac{c\phi_0}{4\pi D} \frac{e^{-Kd}}{d}. \quad (2)$$

In order to estimate the depth at which blood is observable with fluorescence, we assume 1 ml of leaked blood in a 80 kgm patient with the recommended ICG dosage of 400 $\mu$gm/kgm(BW). The corresponding value of N0=5×1015 ICG atoms in Eq. (1) with the parameters mentioned above results in the plot of maximum photon surface flux versus blood depth shown in FIG. 7. The photon rate is computed for a 12×12 $\mu$m CCD pixel with a dark durrent of 5e−/sec shown in the graph. These results indicated that ICG in blood may be observable at depths of 8 cm–10 cm depths in tissue.

Figure 13:
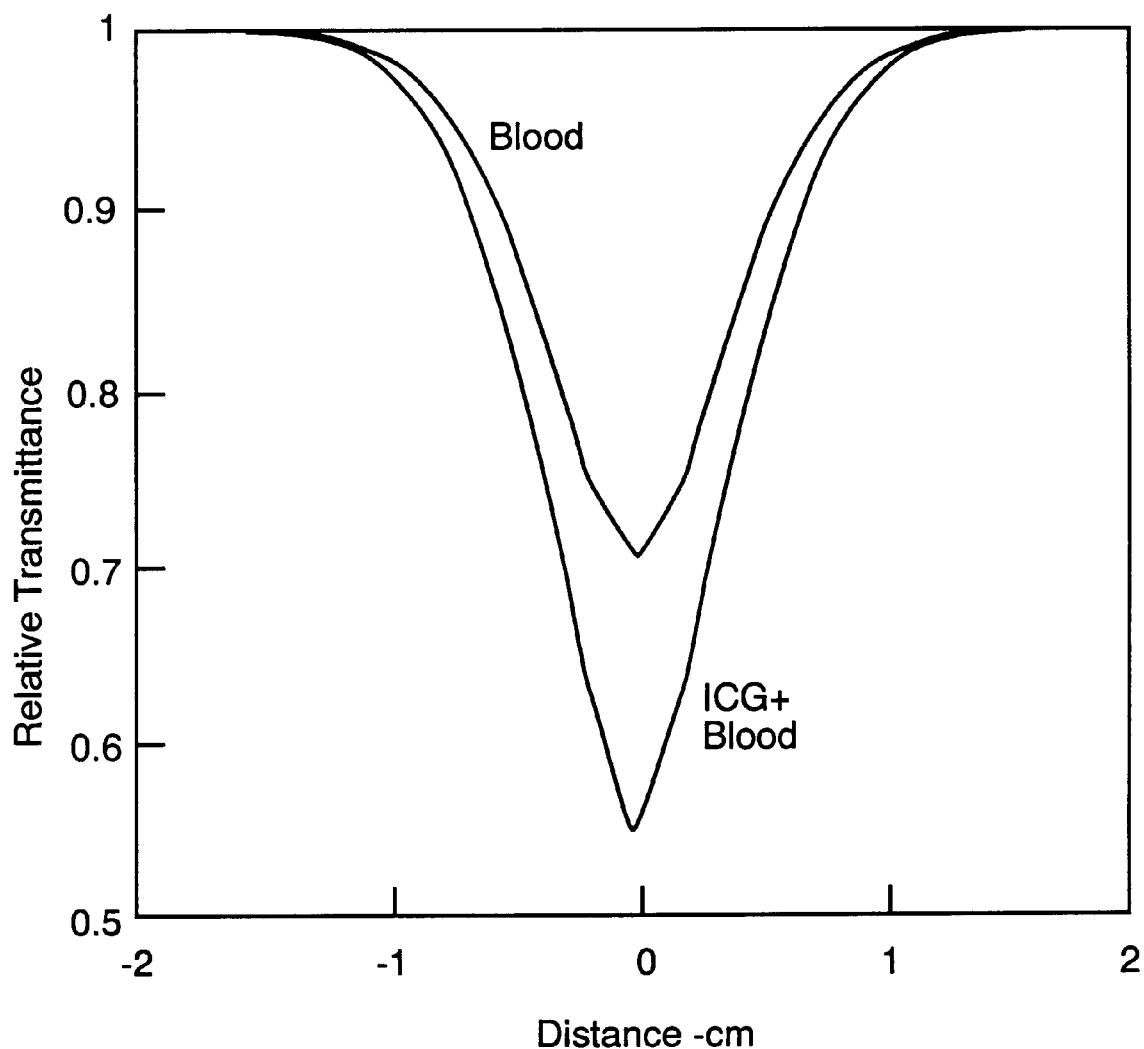
FIG. 13 is a chart of simulated ICG imaging through tissue with and without ICG serum mixture.
Figure 14:
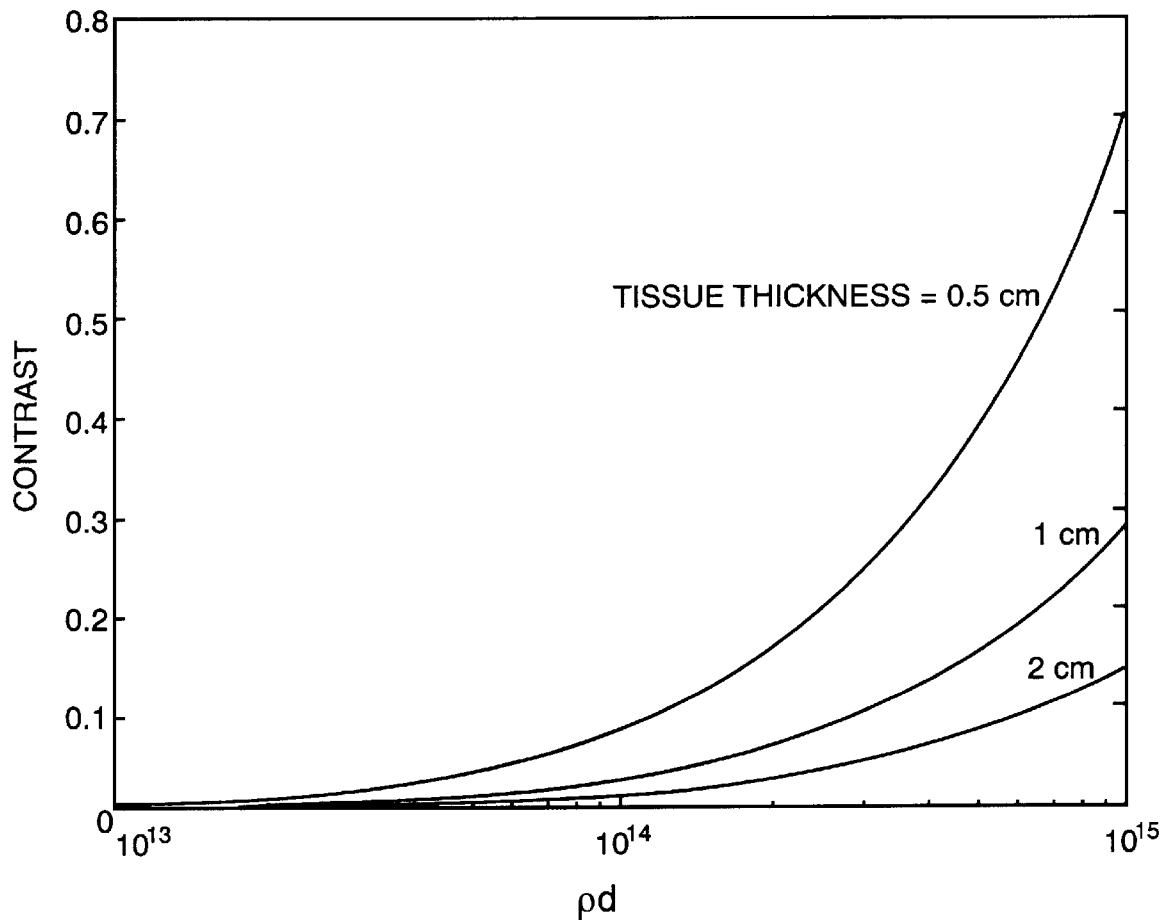
FIG. 14 is a chart of dye concentration versus contrast for different tissue thicknesses.
Figure 15:
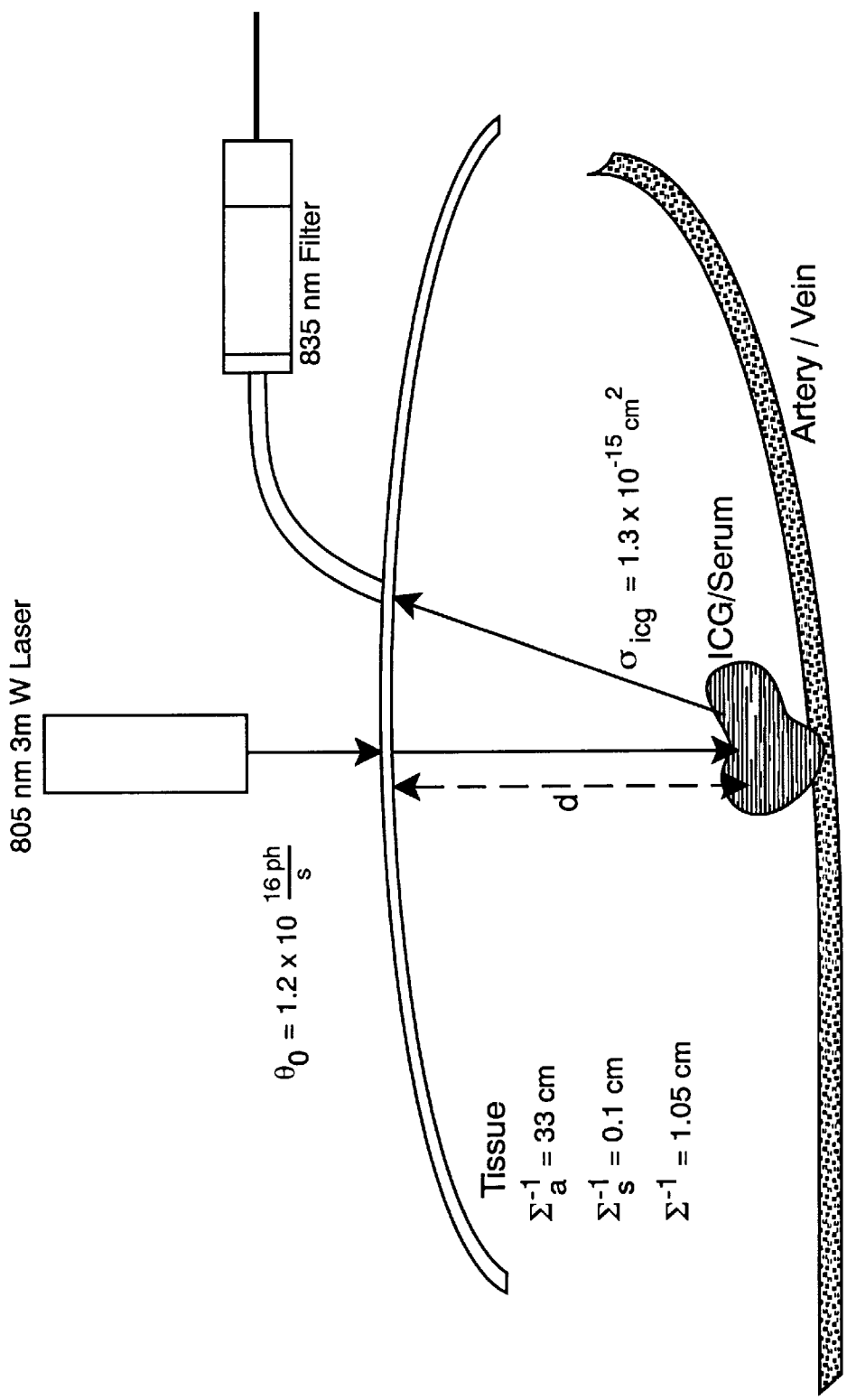
FIG. 15 is an illustration of the test set-up to detection of internal bleeding with fluorescence.
Figure 16:
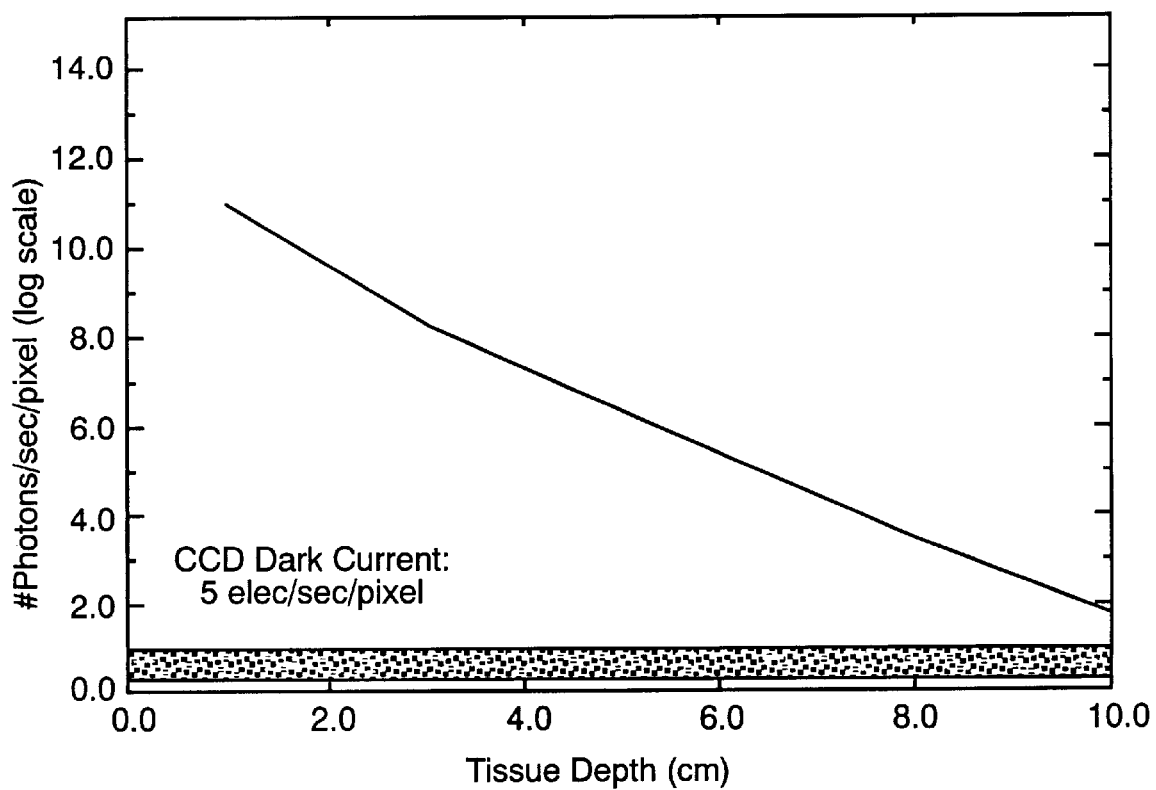
FIG. 16 is a chart of photon rate at tissue depth.

The results of our Monte Carlo simulations in FIG. 13 prove that image processing is required for effective near-IR cancer detection. We have defined two classes of algorithms as 1) deblurring to remove photon scattering effects seen in FIG. 3 and 2) discrimination to detect the presence of a tumor-specific contrast agent or endogenous chromophore. Both algorithm types will be optimized to take advantage of the multispectral measurements described above.

During the past year we have derived deblurring filters to remove the effects of IR photon scattering in normal breast tissue. We are investigating the application of a set of interactive depth-dependent, multispectral deblurring filters for refocusing. An alternative approach is the derivation of the deblurring filter set from an 'impulse response' derived from the contrast agent of the structures at the tumor depth. An example of data-adaptive deblurring is obtained by multispectral data fusion (800 nm and 900 nm) appropriate to this experiment.

Figure 17:
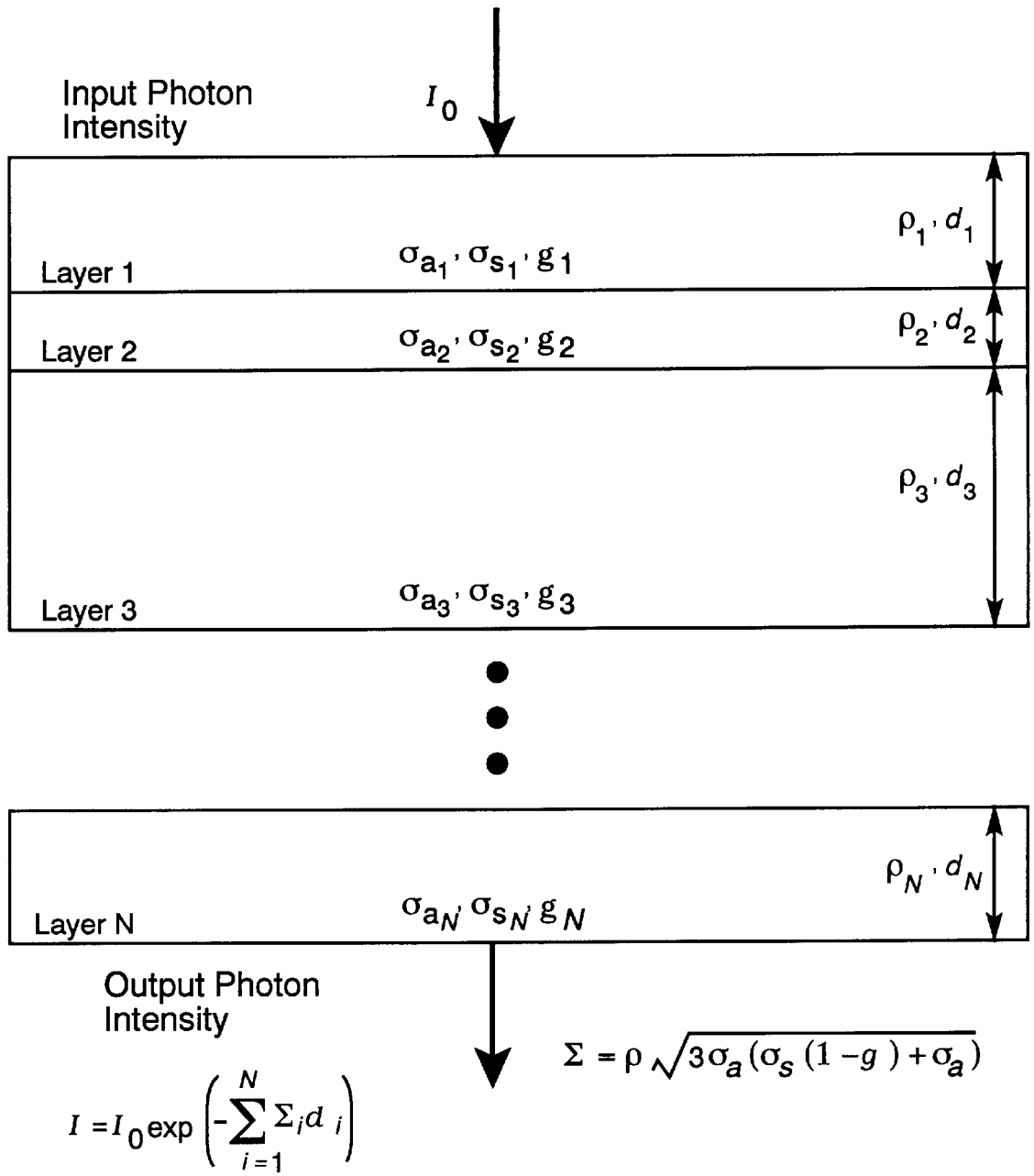
FIG. 17 is a chart of multilayer diffusion of tissue.

We have also begun the development of discrimination algorithms, which input multispectral near-IR images and the spectra of injected and endogenous discrimination agents. In order to derive multispectral discrimination algorithms, we model the tissue as $\underline{N}$ layers of different materials with lolecualr number density pj ad thickness dj, j=1, . . . , N. The diffusion approximation for photon propagation relates the input and output intensities for the jth layer as $$I_{out}(\lambda) = I_{in}(\lambda) e^{-\Sigma j(\lambda) dj}, \quad (3)$$

where $\Sigma j$ is the extinction coefficient for the jth layer given by $$\sum\nolimits_j = \rho_j \sqrt{3\sigma_{a_j}(\sigma_{s_j}(1-g_j) + \sigma_{a_j})} \equiv \rho_j \sigma_j, \quad (4)$$

with $\sigma\alpha$(s) the absorption (scattering) cross section (cm2) and gj the Henyey-Greenstein scattering parameter. The diffusion approximation for multilayered media in FIG. 17 then results in a relationship between input and output light intensities given by $$-\log \frac{I_{out}(\lambda)}{I_{in}(\lambda)} = \sum_{j=1}^{N} \sigma_j(\lambda) \rho_j d_j. \quad (5)$$

Figure 18:
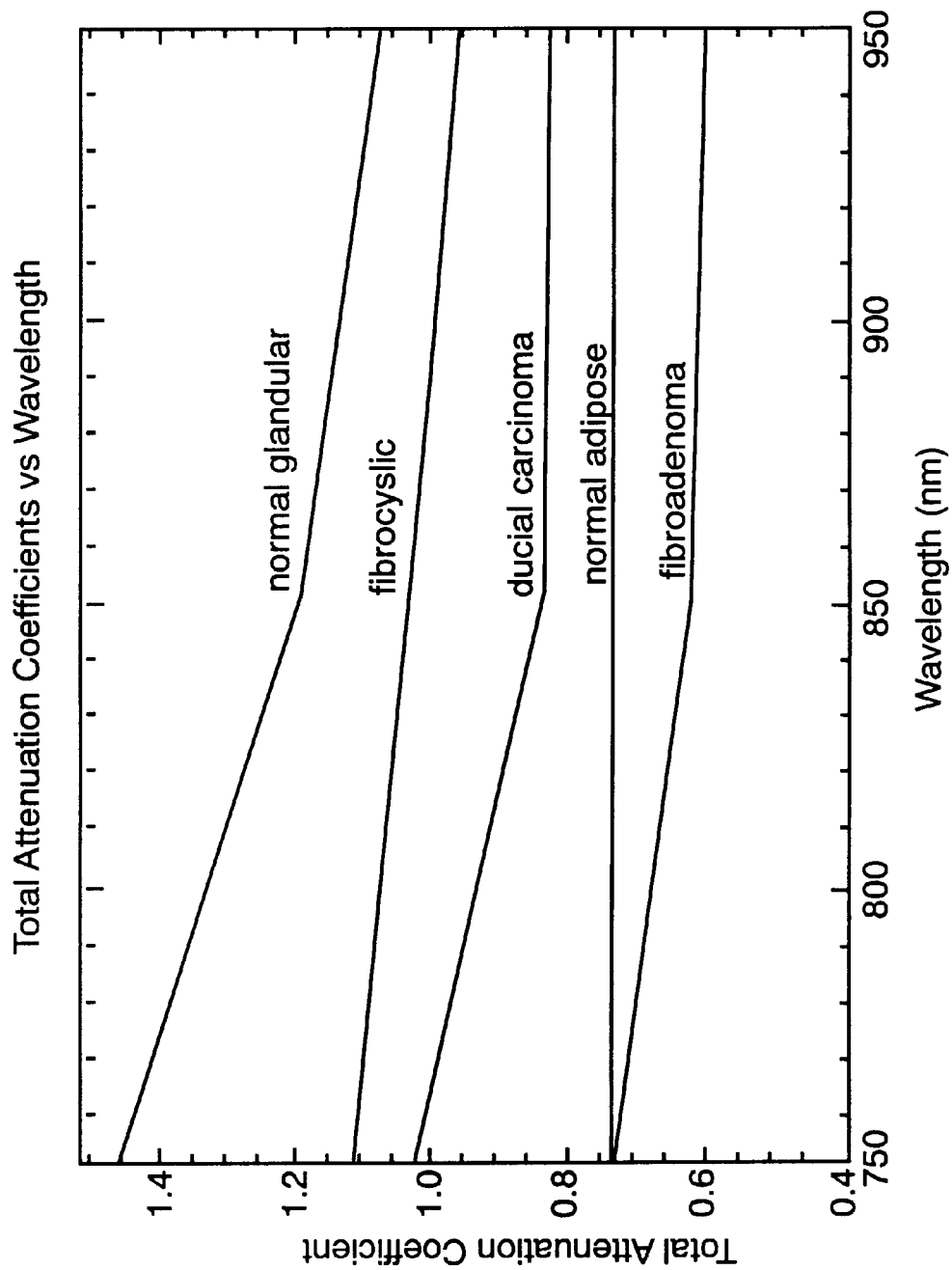
FIG. 18 is a chart of total allenuation coefficients vs. wavelength.

Equation (5) relates the measured intensities I($\lambda$) to unknown effective concentrations pjdj through tinput effective cross sections σj($\lambda$). From the measurements of σa, σs, and g in Ref.[13] and Eq. 4, we obtain the coefficient σ($\lambda$) for various breast tissue types shown in FIG. 18. The extinction coefficients for Hb, Hb02, and ICG in serum are obtained. The inversion of Eq. (5) for the effective concentration of each component from multispectral images defines a detection algorithm for tumor-specific quantities. The algorithm outputs a measure pd of each discrimination agent at each pixel in the field of view.

We have done preliminary image processing using the model in Eqs. (3) and (4). For example the log ratio of images at two different wavelengths, $\lambda 1$ and $\lambda 2$ yields an expression for a single layer $$-\log \frac{I_{out}(\lambda_1)}{I_{out}(\lambda_2)} = (\sigma(\lambda_1) - \sigma(\lambda_2))\rho d. \quad (6)$$

If the differences of cross sections ($\Delta\sigma$) between $\lambda 1$, and $\lambda 2$ for cancerous tissue is different that for normal tissue for comparable pd-values, the log ratio image will discriminate the tumor.

We have applied the above algorithm to three-wavelength inversions for the in-vitro detection of ICG in tissue samples. Assuming two extinction coefficients for tissue with and without ICG, we obtain the expression $$-\log \frac{I_{out}(\lambda)}{I_{in}(\lambda)} = \rho_t d_t \sigma_t(\lambda) + \rho_{icq} d_{icg} \sigma_{icg}(\lambda), \quad (7)$$

where σt(icg), pt(icg), and dt(icg) are the cross section density, and thickness of the tissue (ICG) layer. The input functions σicg($\lambda$) and σt($\lambda$) were obtained.

We recognize that the use of immunoconjugates can enhance the sensitivity of IR imaging in tissues. A contrast agent can be actively applied to a specific site through antibody selectivity. The labeling of mono-clonal antibody with an infrared-sensitive dye will result in an increased tumor contrast.

In the case of breast cancer imaging, the ICG-labeled antibodies are against tumor-associated or -specific (if available) antigens. Antigenic markers include proteoglycans, glycoproteins, and glycolipids on the tumor cell plasma membrane. These markers may allow the discrimination between cancerous and non-cancerous tissue even in the presence of background absorption and fluorescence. Total antibody specificity for these antigens is not a requirement.

Cancer is a progressive disease associated with many biochemical changes, including the alteration of the cell surface over time. For example, the loss of cell adhesion molecules (CAMs) at the sdurface results in the loss of cell-cell adhesion and increased migratory ability. Antibodies against these stage-dependent markers should enable the discrimination of transformation phases in the development of malignancy. Since tumor malignancy occurs after angiogenesis, immunoconjugates which recognize markers prevalent in the hyperplasia (pre-angiogensis) stage of cancer development should provide a basis for the discrimination between malignant and benign tumors.

In order to attach ICG to the antibody, chemical modification of the molecule is required to create a group reactive with the primary amines on the protein. However, these reactions must not disturb the rings which are responsible for the near-IR ICG spectrum. To conjugate the ICG molecule to an antibody, the —SO2—OH group must be activated via s-halo-de-hydroxylation $$R\text{—}SO_3H + PCl_5 \rightarrow R\text{—}SO_2\text{—}Cl, \quad (8)$$

where R is the portion of the ICG molecule not shoen [29]. Alternatively, in Eq.(8) we can use thionyl chloride (SOC12) of phosphorous trichloride (PC13) in place of phosphorous pentachloride (PC15). The product, a sulfonylchloride form of ICG, is now susceptible to nucleophilic attack by a primary amine group of the protein. The reaction in Eq.(9) depicts the s-amino-de-chlorination reaction which displaces the leaving chlorine atom, $$R\text{—}SO_2\text{—}Cl + :NH_2\text{—}R' \rightarrow R\text{—}SO_2\text{—}NH\text{—}R', \quad (9)$$

where R' is the momo-clonal antibody of interest [30]. The product in reaction Eq. (9) is the desired immunoconjugate. Experimental parameters such as reactant concentrations, pH, and temperature yielding the most productive reaction need to be determined.

While the invention has been described in its presently preferred embodiment it is understood that the words which have been used are words of description rather than words of limitation and that changes within the purview of the appended claims may be made without departing from the scope and spirit of the invention in its broader aspects.

We claim:

1. A non-invasive multispectral imaging system which comprises:

a transilluminating radiating means that illuminates soft tissues that have been treated with a contrast agent using first and second near-IR illuminating signals to produce thereby a first and second near-IR multispectral image;

a means for optically combining the first and second near-IR multispectral images into a combined tissue image; and a means for processing the combined tissue image to detect cancer and tumors.

2. A non-invasive multispectral imaging system as defined in claim 1 wherein said radiating means comprises a diode laser system that emits the first and second near-IR illuminating signals with wavelengths selected from a range between 750 nm and 1,000 nm.

3. A non-invasive multispectral imaging system as defined in claim 1 wherein said optically combining means comprises a CCD camera which is placed in a location with the soft tissues between the CCD camera and the transilluminating means.

4. A non-invasive multispectral imaging system as defined in claim 3 further comprising a means for injecting IR dyes and endogenous chromophores and fluophores to facilitate tumors, cancer and internal bleeding.

5. A non-invasive multispectral imaging system as defined in claim 4 wherein said IR dyes comprise indocyanine green (ICG).

6. A non-invasive multispectral imaging process which comprises the steps of:

transilluminating radiating signals that illuminate soft tissues that have been treated with a contrast agent using a source of first and second near-IR illuminating signals to produce thereby a first and second near-IR multispectral image;

optically combining the first and second near-IR multispectral images into a combined tissue image; and processing the combined tissue image to detect cancer and tumors.

7. A non-invasive multispectral imaging process as defined in claim 6 wherein said radiating step comprises a use of a diode laser system that emits the first and second near-IR illuminating signals with wavelengths selected from a range between 750 nm and 1,000 nm.

8. A non-invasive multispectral imaging process as defined in claim 7 wherein said optically combining step comprises using a CCD camera which is placed in a location with the soft tissues between the CCD camera and the source of first and second near-IR illuminating signals.

9. A non-invasive multispectral imaging process as defined in claim 8 further comprising injecting IR dyes and endogenous chromophores and fluophores to facilitate tumors, cancer and internal bleeding.

10. A non-invasive multispectral imaging process as defined in claim 9 wherein said IR dyes comprise indocyanine green (ICG).

* * * * *